(12) United States Patent
Daste et al.

(10) Patent No.: US 6,218,403 B1
(45) Date of Patent: Apr. 17, 2001

(54) ANTITHROMBOTIC AND ANTIATHEROGENIC PHARMACEUTICAL COMPOSITION INCLUDING A THIENOPYRIDINE DERIVATIVE AND AN HMG-COA-REDUCTASE INHIBITOR

(75) Inventors: Georges Daste, Bordeaux; Jean Marc Herbert, Tournefeuille, both of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/230,299

(22) PCT Filed: Jul. 21, 1997

(86) PCT No.: PCT/FR97/01353

§ 371 Date: Jan. 22, 1999

§ 102(e) Date: Jan. 22, 1999

(87) PCT Pub. No.: WO98/04259

PCT Pub. Date: Feb. 5, 1998

(30) Foreign Application Priority Data

Jul. 26, 1996 (FR) .................................. 96 09474

(51) Int. Cl.⁷ .................................. A61K 31/44
(52) U.S. Cl. .................................. 514/301; 514/824
(58) Field of Search .................................. 514/301, 824

(56) References Cited

U.S. PATENT DOCUMENTS 5,945,432 * 8/1999 Bednar et al. .................. 514/301

FOREIGN PATENT DOCUMENTS

| 0 373 507 | 12/1989 | (EP). |
| 0 472 449 | 7/1991 | (WO). |
| WO95/11898 | 10/1993 | (WO). |
| WO95/13063 | 5/1995 | (WO). |

OTHER PUBLICATIONS

International Journal of Tissue Reactions, vol. 13, No. 3, pp. 124–129, 1991.
Fibrinolysis, vol. 7, No. 1, pp. 23–30, 1993.
Diabete & Metabolisme, vol. 21, pp. 139–146, 1995.

* cited by examiner

Primary Examiner—Frederick Krass
(74) Attorney, Agent, or Firm—Michael D. Alexander; Paul E. Dupont

(57) ABSTRACT

The present invention relates to a pharmaceutical composition containing:

(a) a thienopyridine derivative of formula

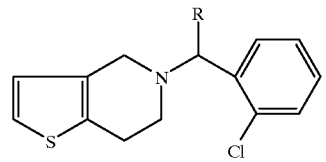

(I)

in which R is hydrogen or a $(C_1$–$C_4)$alkoxycarbonyl group, or one of its pharmaceutically acceptable salts; and (b) an HMG-CoA reductase inhibitor.

18 Claims, No Drawings

ANTITHROMBOTIC AND ANTIATHEROGENIC PHARMACEUTICAL COMPOSITION INCLUDING A THIENOPYRIDINE DERIVATIVE AND AN HMG-COA-REDUCTASE INHIBITOR

This application is a 371 of PCT/FR97/01353, filed Jul. 21, 1997.

The present invention relates to a pharmaceutical composition containing as active principle a combination of a thienopyridine derivative and an HMG-CoA reductase inhibitor.

More especially, the subject of the present invention is a pharmaceutical composition containing (a) a thienopyridine derivative of formula

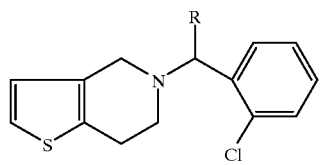

(I)

in which R is hydrogen or a $(C_1–C_4)$alkoxycarbonyl group, or one of its pharmaceutically acceptable salts; and (b) an HMG-CoA reductase inhibitor.

The thienopyridine derivatives of formula (I) are known to be potent platelet aggregation inhibitors, acting via a mechanism of action which distinguishes them from other platelet aggregation inhibitors.

These compounds, in particular 5-(2-chlorobenzyl)-4,5,6,7-tetrahydrothieno[3,2]pyridine of formula (I), R=hydrogen, hereinafter designated by its international nonproprietary name (INN) "ticlopidine", used in hydrochloride form, and (+)-[methyl (S)-α-(2-chlorophenyl)-4,5,6,7-tetrahydrothieno[3,2-c]-pyridin-5-ylacetate] of the formula (I), R=methoxycarbonyl, hereinafter designated by its INN "clopidogrel", used in hydrogen sulphate form, are exceptional antithrombotic agents (Gent et al., Lancet, 1989, 8649, 1215–1220—J-M. Herbert et al., Cardiovasc. Drug Rev., 1993, 11, 180–188).

It has now been found that, by combining a thienopyridine derivative of formula (I) and an HMG-CoA reductase inhibitor, a potentiation of the anti-atherogenic power of the two components is observed, more especially an additive and/or synergistic activity of the two active principles with respect to the proliferation of rabbit artery smooth muscle cells.

It has also been found that the combination of a thienopyridine derivative of formula (I) and an HMG-CoA reductase inhibitor is provided with an additive and/or synergistic activity of the two active principles in an animal model of arterial thrombosis which is predictive of a preventive or curative clinical antithrombotic activity.

Thus, according to the present invention, a therapeutically effective dose of a thienopyridine derivative of formula (I), or of one of its pharmaceutically acceptable salts [Component (a)], is combined with a therapeutically effective dose of an HMG-CoA reductase inhibitor [Component (b)] so as to prepare pharmaceutical compositions intended for treating or preventing atherosclerosis, postangioplasty restenosis or the thrombotic complications resulting therefrom.

In a dosage unit containing the combination of a thienopyridine of formula (I) and an HMG-CoA reductase inhibitor, the therapeutically effective dose of Component (a) can vary from 10 to 250 mg of active principle (calculated as free base or as salt), whereas the therapeutically effective dose of Component (b) can vary from 2 to 50 mg of active principle.

According to the present invention, the thienopyridine derivative of formula (I) is preferably selected from ticlopidine and the pharmaceutically acceptable salts, in particular ticlopidine hydrochloride, and clopidogrel and the pharmaceutically acceptable salts, in particular clopidogrel hydrogen sulphate.

When Component (a) in a dosage unit is ticlopidine hydrochloride, the amount of this active principle in the dosage unit can advantageously vary from 100 to 250 mg, the said amount of active principle preferably being 150, 175, 200, 225 or 250 mg per dosage unit.

When in the dosage unit Component (a) is clopidogrel hydrogen sulphate, the amount of this active principle in the dosage unit can advantageously vary from 10 to 75 mg (calculated as free base), the said amount of active principle preferably being 25, 35, 50, 65 or 75 mg as free base per dosage unit.

According to the present invention, the HMG-CoA reductase inhibitor is advantageously a compound selected from (I) the naphthalene derivatives of formula (II)

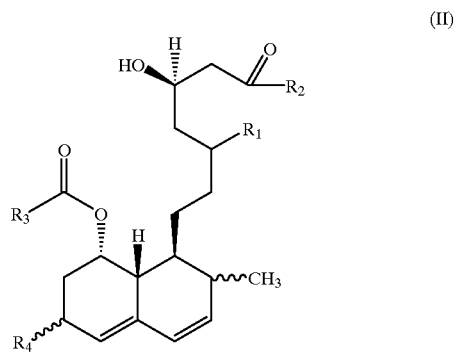

(II)

in which $R_1$ and $R_2$ are a hydroxyl group or alternatively together form an oxygen atom, $R_3$ is a $(C_1–C_{10})$alkyl, $(C_3–C_{10})$cycloalkyl, $(C_2–C_{10})$alkenyl, phenyl or phenyl$(C_1–C_3)$alkyl group and $R_4$ is hydrogen or a methyl or hydroxyl group;

(ii) the pharmaceutically acceptable salts of the compounds of formula (II) in which $R_1$ and $R_2$ are hydroxyl;

(iii) the indole derivatives of formula (III)

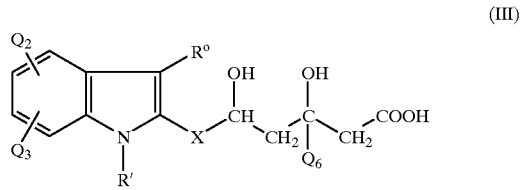

(III)

in which one of the substituents R° and R' is a group of structure

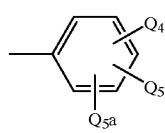

in which $Q_4$ is a hydrogen, chlorine or fluorine atom or a $(C_1-C_4)$alkyl, $(C_1-C_4)$alkoxy (but other than t-butoxy), trifluoromethyl, phenoxy or benzyloxy group, $Q_5$ is a hydrogen, chlorine or fluorine atom or a phenoxy or benzyloxy group and $Q_{5a}$ is a hydrogen, chlorine or fluorine atom or a methyl, ethyl, methoxy or ethoxy group;

and the other substituent R° and R' is a primary or secondary $(C_1-C_6)$alkyl, $(C_3-C_6)$cycloalkyl, benzyl, 2-phenylethyl or 3-phenylpropyl group;

$Q_2$ is a hydrogen, fluorine or chlorine atom or a $(C_1-C_4)$alkyl, $(C_3-C_6)$cycloalkyl, $(C_1-C_4)$alkoxy (but other than t-butoxy), trifluoromethyl, phenoxy or benzyloxy group;

$Q_3$ is a hydrogen, chlorine or fluorine atom or a $(C_1-C_3)$alkyl, $(C_1-C_3)$alkoxy, phenoxy or benzyloxy group;

X is a methylene, ethylene or 1,3-propylene group;

$Q_6$ is a hydrogen atom or a $(C_1-C_3)$alkyl group; with the limitation that
(1) $Q_5$ and $Q_{5a}$ are hydrogen when $R_4$ is hydrogen,
(2) $Q_{5a}$ is hydrogen when $Q_5$ is hydrogen,
(3) $Q_4$ and $Q_3$ are not at the same time a trifluoromethyl, phenoxy or benzyloxy group,
(4) $Q_3$ is hydrogen when $Q_2$ is hydrogen,
(5) $Q_2$ and $Q_3$ are not at the same time a trifluoromethyl, phenoxy or benzyloxy group;

(iv) the pharmaceutically acceptable esters of the compounds of formula (III),
(v) the pharmaceutically acceptable salts of the compounds of formula (III),
(vi) the δ-lactones of the compounds of formula (III),
(vii) the tetrazole derivatives of formula (IV)

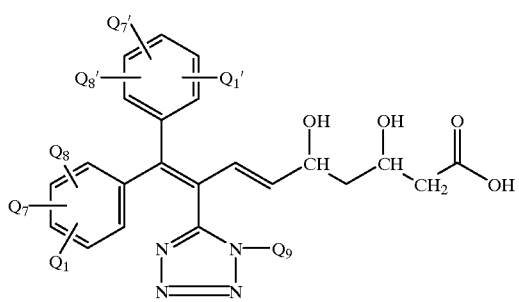

(IV)

in which
$Q_1$ and $Q_1'$ are hydrogen, a halogen or a $(C_1-C_4)$alkyl, $(C_1-C_4)$alkoxy or trifluoromethyl group;
$Q_7$, $Q_7'$, $Q_8$, and $Q_8'$ are hydrogen, a halogen or a $(C_1-C_4)$alkyl or $(C_1-C_4)$alkoxy group;
$Q_9$ is hydrogen or a $(C_1-C_4)$alkyl, $(C_1-C_4)$alkoxyalkyl or (2-methoxyethoxy)methyl group;
(viii) the pharmaceutically acceptable salts of the compounds of formula (IV), (ix) the δ-lactones of the compounds of formula (IV),
(x) the pyridine derivatives of formula (V)

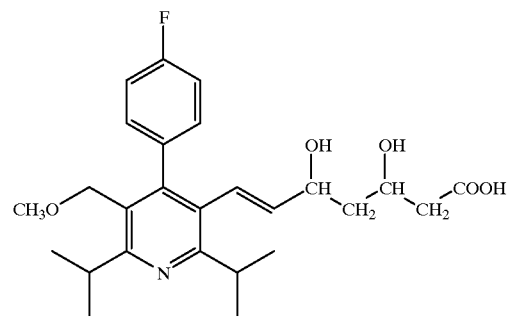

(V)

(xi) the pharmaceutically acceptable salts of the compounds of formula (V),
(xii) the δ-lactones of the compounds of formula (V),
(xiii) the pyrrole derivatives of formula (VI)

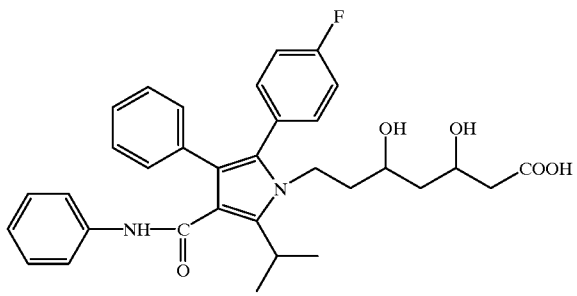

(VI)

(xiv) the pharmaceutically acceptable salts of the compounds of formula (VI),
(xv) the δ-lactones of the compounds of formula (VI).

The compounds corresponding to the formulae (II) to (VI) possess at least two chiral carbons, it also being possible for the compounds (II) to (V) to be present in cis or trans form. Component (b) can be selected from the isomers of the compounds (II) to (VI) or the mixtures thereof.

The compounds (II) to (VI) are described in the literature. More especially, the indole derivatives of formula (III) are described in WO 84/02131, the tetrazole derivatives of formula (IV) are described in EP 658550, the pyridine derivatives of formula (V) are described in DE 4040026 and the pyrrole derivatives of formula (VI) are described in EP 409281.

The naphthalene compounds of formula (II) in which $R_4$ is hydrogen or a methyl group are described in EP 33538, or may be prepared either according to the method described in this document or by partial synthesis or, in some cases, by total synthesis, for example in the case of the synthesis of mevastatin (J. Am. Chem. Soc., 1981, 6538; ibid. 1982, 4251) or of lovastatin (Tetrahedron Letters. 1983, 24, 1811). Simvastatin is also described in EP 33538.

The naphthalene compounds of formula (II) in which $R_4$ is hydroxyl are described in GB 2,077,264. Among these compounds, pravastatin, used in the form of the sodium salt, constitutes an especially advantageous Component (b).

Among the indoles of formula (III), the compound having this formula in which R° is 4-fluorophenyl, R' is isopropyl, X is ethylene and $Q_2$, $Q_3$ and $Q_6$ are hydrogen, in its racemic or optically active (E) form, and its pharmaceutically acceptable salts, constitute an especially advantageous Component (b) for the pharmaceutical compositions of the present invention.

Among the tetrazole derivatives of formula (IV), the compound having this formula in which $Q_1$ and $Q_1'$ are each a fluorine atom, $Q_7$, $Q_7'$, $Q_8$ and $Q_8'$ are hydrogen and $Q_9$ is a methyl group, in its racemic or optically active, preferably ($\beta R, \delta S$), (E) form, and its pharmaceutically acceptable salts, in particular with an amino acid, also constitute an especially advantageous Component (b) for the pharmaceutical compositions of the present invention.

The pyridine derivative of formula (V), in its racemic or optically active, preferably ($\beta R, \delta S$), (E) form, or cerivastatin, and its pharmaceutically acceptable salts, constitute another advantageous Component (b) for the pharmaceutical compositions of the present invention.

The $\delta$-lactone of the pyrrole derivative of the formula (VI), known as atorvastatin, constitutes an advantageous Component (b) for the pharmaceutical compositions of the present invention.

According to an advantageous aspect, the compositions of the present invention contain ticlopidine hydrochloride as Component (a) and simvastatin or pravastatin sodium as Component (b). Preferably, such compositions contain from 100 to 250 mg of ticlopidine hydrochloride and from 10 to 40 mg of simvastatin or of pravastatin sodium.

According to another advantageous aspect, the compositions of the present invention contain clopidogrel hydrogen sulphate as Component (a) and simvastatin or pravastatin sodium as Component (b). Preferably, such compositions contain from 10 to 75 mg (calculated as free base) of clopidogrel hydrogen sulphate and from 10 to 40 mg of simvastatin or prevastatin sodium.

The combinations of active principles according to the invention were subjected to pharmacological studies.

Experiments were carried out to implement the test for proliferation of vascular wall muscle cells occurring following a de-endothelialization of the carotid artery of rabbits. Briefly, New Zealand rabbits weighing 2.5–3 kg were fed with a synthetic feed containing 2% of cholesterol and 6% of groundnut oil. The animals were treated orally with clopidogrel (5 mg/kg/d). The animals were simultaneously treated orally with simvastatin (5 mg/kg/d). The compounds were administered 2 days before lesion of the endothelium and daily for 2 weeks. Myointimal proliferation of the rabbit carotid was induced by drying in the air according to the method described previously (Fishman et al., Lab. Invest., 1975, 32, 339–347; Herbert et al., 1993, 13, 171–1179). The animals were anaesthetized intravenously with pentobarbital sodium (30 mg/kg, i.v.) and the left carotid was isolated. A hypodermic syringe (27 gauge) was inserted into a proximal portion of the artery and also into a distal portion. The arterial segment thus isolated was emptied of its blood and washed with physiological saline, and endothelial injury was induced by passing a stream of dry air through it (240 ml/min for 5 minutes). The needles were then withdrawn, the blood circulation was re-established and the incision was closed up. Fourteen days after the lesion, the animals were anaesthetized (pentobarbital sodium, 30 mg/kg, i.v.). The arterial segment was isolated, rinsed with physiological saline and incubated for 18 hours in 10% formaldehyde solution. The arterial segments were then dehydrated in ethanol, included in paraffin, cut with a microtome and stained with haematoxylin-eosin. The medial and intimal surfaces were quantified by image analysis (Biocom Imagenia 5000, Lyons, France).

The results shown in TABLE 1 indicate that clopidogrel and simvastatin (5 mg/kg/d) administered orally daily in rabbits inhibit the proliferation of smooth muscle cells following a lesion of the endothelium with a stream of air.

In all cases, the joint administration of clopidogrel and simvastatin resulted in a significant synergistic effect with respect to the proliferation of smooth muscle cells. That is to say, when the products were administered in combination, the antiproliferative effect obtained was always greater than the simple sum of the effects of the two test products taken separately.

TABLE 1

Effect of the products alone or in combination with respect to myointimal proliferation following a lesion of the vascular endothelium.

TABLE 1

| Products | Doses | % inhibition of myointimal proliferation |
|---|---|---|
| Clopidogrel | 5 mg/kg/d | 31 ± 4% |
| Simvastatin | 5 mg/kg/d | 48 ± 7% |
| Clopidogrel + simvastatin | 5 + 5 mg/kg/d | 92 ± 9% |

The values in the table are mean values ± standard errors (n=10).

Moreover, the antithrombotic effect of the combination according to the invention was demonstrated in a test for formation of a thrombus on a silk thread present in an arteriovenous shunt implanted between the carotid artery and the jugular vein of rabbits, as described by Umetsu et al. (Thromb. Haemostas., 1978, 39, 74–83). New Zealand rabbits weighing 2.5 to 3 kg were treated. The animals were anaesthetized by subcutaneous administration of pentobarbital sodium (30 mg/kg). Two polyethylene tubes 12 cm in length (internal diameter: 0.6 mm; external diameter: 0.9 mm), attached by a central portion 6 cm in length (internal diameter: 0.9 mm) containing a silk thread 5 cm in length, were placed between the right carotid artery and the left jugular vein. The central portion of the shunt was then placed in position, and thereafter withdrawn after 20 minutes of circulation of blood in the shunt. The weight of the thrombus present on the silk thread was then determined.

In the same manner as in the case of the effects measured with respect to the proliferation of smooth muscle cells following a lesion of the endothelium by a stream of air, the antithrombotic activity of clopidogrel was potentiated by a combination with simvastatin. Under these conditions, and as with respect to the proliferation of smooth muscle cells, a significant synergistic effect was observed. The results obtained are recorded in TABLE 2 below.

TABLE 2

Effect of the products alone or in combination with respect to the formation of an arterial thrombus on a silk thread implanted in an arteriovenous shunt in rabbits.

TABLE 2

| Products | Doses | % inhibition of thrombosis |
|---|---|---|
| Simvastatin | 5 mg/kg | 15 ± 4% |
| Clopidogrel | 5 mg/kg | 34 ± 4% |

TABLE 2-continued

| Products | Doses | % inhibition of thrombosis |
| --- | --- | --- |
| Clopidogrel + simvastatin | 5 + 5 mg/kg | 72 ± 5% |

The values in the table are mean values ± standard errors (n=5).

The combination of the thienopyridine and the HMG-CoA reductase inhibitor is formulated in pharmaceutical compositions which can be used orally or parenterally, in particular orally, mixed with traditional pharmaceutical excipients.

The said pharmaceutical compositions which are the subject of the present invention preferably take the form of dosage units containing a predetermined amount of the active principles, as is specified above. The single-dose forms for oral administration comprise tablets, gelatin capsules, powders, granules and microgranules.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other suitable materials, or can alternatively be treated in such a way as to have sustained or delayed activity and to release a predetermined amount of active principle continuously.

A gelatin capsule preparation is obtained by mixing the active ingredient with a diluent and pouring the mixture obtained into soft or hard gelatin capsules.

The active principle may also be formulated in the form of microcapsules, where appropriate with one or more vehicles or additives.

The active principles of the combinations can also take the form of a complex with a cyclodextrin, for example α-, β- or γ-cyclodextrin, 2-hydroxypropyl-β-cyclodextrin or methyl-β-cyclodextrin.

In the formulation of the combinations of the active principles for the preparation of the pharmaceutical compositions according to the present invention, the nature of Components (a) and (b) of the combinations will be borne in mind. Component (a), namely the thienopyridine, is preferably used in the form of an addition salt with pharmaceutically acceptable acids. For example, preferred Components (a) are ticlopidine hydrochloride and clopidogrel hydrogen sulphate, which are acidic compounds.

Normally, the thienopyridines, in the form of their addition salts with pharmaceutically acceptable acids, are not chemically incompatible with HMG-CoA reductase inhibitors. However, some of the latter are used in the form of salts with alkali metals, as, for example, in the case of pravastatin sodium. It is hence preferable to keep the active principles separated according to techniques which are well known from the literature.

Thus, the pharmaceutical dosage form containing the combination of the thienopyridine and the HMG-CoA reductase inhibitor can be presented, for example, as a transparent or opaque gelatin capsule containing two tablets, of which one contains the thienopyridine and the other contains the HMG-CoA reductase inhibitor. This presentation has the advantage of using the two active principles constituting the combination in the pharmaceutical dosage form which is commonly used, it being possible for each tablet to be coated with a film which permits either the immediate release of the two active principles or a programmed release over different times.

Another presentation can envisage gelatin capsules containing a mixture of microgranules, of which some contain the thienopyridine and the others contain the HMG-CoA reductase inhibitor, it being possible for the said microgranules to be coated with a film permitting the immediate or programmed release of the active principles.

The pharmaceutical dosage form containing the combination according to the present invention can be presented as a double- or triple-layer tablet, more especially as tablets prepared by subjecting the products to more than one compression. The outcome of such a dosage form can be either a two-layer tablet, the layers being separated, for example, by a film, or a tablet inside another tablet, the two parts being, where appropriate, coloured differently.

Another pharmaceutical dosage form of the combination according to the present invention can be presented as a double gelatin capsule, consisting of an inner gelatin capsule containing one of the two components and an outer gelatin capsule containing the first capsule and the other component. In this case, it is preferable for the inner capsule to contain the HMG-CoA reductase inhibitor and the outer capsule to contain the thienopyridine. A pharmaceutical dosage form of this type is described in U.S. Pat. No. 5,310,555.

In the combinations according to the present invention, the pharmaceutical dosage forms of the present invention preferably contain 250 mg of ticlopidine hydrochloride and 20 mg of simvastatin or of pravastatin sodium; 250 mg of ticlopidine hydrochloride and 15 mg of simvastatin or 15 mg of pravastatin sodium; 200 mg of ticlopidine hydrochloride and 15 mg of simvastatin or 15 mg of pravastatin sodium; 175 mg of ticlopidine hydrochloride and 20 mg of simvastatin or of pravastatin sodium; 175 mg of ticlopidine hydrochloride and 15 mg of simvastatin or of pravastatin sodium; 250 mg of ticlopidine hydrochloride and 10 mg of simvastatin or of pravastatin sodium; 200 mg of ticlopidine hydrochloride and 10 mg of simvastatin or of pravastatin sodium; 175 mg of ticlopidine hydrochloride and 10 mg of simvastatin or of pravastatin sodium. Combinations containing 250 mg of ticlopidine hydrochloride and 20 mg of simvastatin or of pravastatin sodium can also be envisaged for therapy in the acute situation.

In other combinations according to the present invention, the pharmaceutical dosage forms preferably contain 87.5 mg of clopldogrel hydrogen sulphate and 20 mg of simvastatin or pravastatin sodium; 81.25 mg of clopidogrel hydrogen sulphate and 20 mg of simvastatin or pravastatin sodium; 87.5 mg of clopidogrel hydrogen sulphate and 15 mg of simvastatin or pravastatin sodium; 81.25 mg of clopidogrel hydrogen sulphate and 15 mg of simvastatin or pravastatin sodium; 62.5 mg of clopidogrel hydrogen sulphate and 20 mg of simvastatin or pravastatin sodium; 62.5 mg of clopidogrel hydrogen sulphate and 15 mg of simvastatin or pravastatin sodium; 93.75 mg of clopidogrel hydrogen sulphate and 10 mg of simvastatin or pravastatin sodium; 87.5 mg of clopidogrel hydrogen sulphate and 10 mg of simvastatin or pravastatin sodium; 81.25 mg of clopidogrel hydrogen sulphate and 10 mg of simvastatin or pravastatin sodium; 62.5 mg of clopidogrel hydrogen sulphate and 10 mg of simvastatin or pravastatin sodium. Combinations containing 87.5 mg of clopidogrel hydrogen sulphate and 20 mg of simvastatin or pravastatin sodium can also be envisaged for therapy in the acute situation.

The pharmaceutical compositions of the present invention are especially indicated in the treatment of pathological states such as disorders of the cardiovascular and cerebrovascular system, for instance the thromboembolic disorders associated with atherosclerosis or with diabetes such as unstable angina, stroke, restenosis after angioplasty, endarterectomy or fitting of metallic endovascular prostheses, with rethrombosis after thrombolysis, with infarction, with dementia of ischaemic origin, with peripheral arterial diseases, with haemodialysis and with atrial fibrillation, or alternatively when vascular prostheses or aortocoronary bridges are used, or in relation to stable or unstable angina.

EXAMPLE 1

Ticlopidine/simvastatin Combination (200 mg/20 mg)

1. Double-layer tablet formula

Layer No. 1

| | |
|---|---|
| Ticlopidine (hydrochloride) | 200.00 mg |
| Microcrystalline cellulose | 69.88 mg |
| Modified maize starch | 31.20 mg |
| Povidone | 6.24 mg |
| Citric acid | 3.12 mg |
| Stearic acid | 0.78 mg |
| Magnesium stearate | 0.78 mg |

Layer No. 2

| | |
|---|---|
| Simvastatin | 20.00 mg |
| Butylated hydroxyanisole | 0.04 mg |
| Ascorbic acid | 5.00 mg |
| Citric acid | 2.50 mg |
| Microcrystalline cellulose | 10.00 mg |
| Pregelatinized maize starch | 20.00 mg |
| Lactose | 141.50 mg |
| Magnesium stearate | 1.00 mg |
| Methylhydroxypropylcellulose | 1.65 mg |
| Hydroxypropylcellulose | 1.65 mg |
| Titanium dioxide | 1.50 mg |
| Talc | 0.60 mg |
| Yellow iron oxide | 0.092 mg |
| Red iron oxide | 0.023 mg |

2. Procedure

The ticlopidine granule is prepared by wet granulation.
The simvastatin granule is prepared by wet granulation.
The two granules are compressed on a press permitting the manufacture of double-layer tablets.

EXAMPLE 2

Clopidogrel/simvastatin Combination (50 mg/10 mg)

1. Double-layer tablet formula

Layer No. 1

| | |
|---|---|
| Clopidogrel hydrogen sulphate | 65.00 mg (equivaient to 50 mg of base) |
| Anhydrous lactose | 72.20 mg |
| Modified maize starch | 7.00 mg |
| Macrogel 6000 | 5.00 mg |
| Microcrystalline cellulose | 8.60 mg |
| Hydrogenated castor oil | 2.20 mg |

Layer No. 2

| | |
|---|---|
| Simvastatin | 10.00 mg |
| Butylated hydroxyanisole | 0.02 mg |
| Ascorbic acid | 2.50 mg |
| Citric acid | 1.75 mg |
| Microcrystailine cellulose | 5.00 mg |
| Pregelatinized maize starch | 10.00 mg |
| Lactose | 70.75 mg |
| Magnesium stearate | 0.50 mg |
| Methylhydroxypropylcellulose | 0.825 mg |
| Hydroxypropylcellulose | 0.825 mg |
| Titaniuin dioxide | 0.75 mg |
| Talc | 0.30 mg |
| Yellow iron oxide | 0.046 mg |
| Red iron oxide | 0.0115 mg |

2. Procedures

The clopidogrel granule is prepared by dry granulation (compaction).

The simvastatin granule is prepared by wet granulation.

The two granules are compressed on a press permitting the manufacture of double-layer tablets.

What is claimed is:

1. A synergistic pharmaceutical composition containing:

(a) a thienopyridine derivative of formula

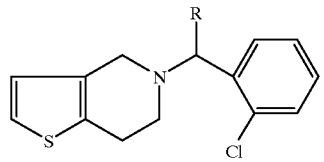

(I)

in which R is hydrogen or a $(C_1-C_4)$alkoxycarbonyl group, or one of its pharmaceutically acceptable salts; and (b) an HMG-CoA reductase inhibitor.

2. A composition according to claim 1, wherein Component (a) is present at a dose of between 10 and 250 mg of active principle and Component (b) is present at a dose of 2 to 50 mg of active principle.

3. A composition according to claim 1, wherein the thienopyridine derivative is ticlopidine hydrochloride.

4. A composition according to claim 3, wherein the amount of ticlopidine hydrochloride in the dosage unit is from 100 to 250 mg.

5. A composition according to claim 1, wherein the thienopyridine derivative is clopidogrel hydrogen sulphate.

6. A composition according to claim 5, wherein the amount of hydrogen sulphate in the dosage unit is from 10 to 75 mg (calculated as free base).

7. A composition according to claim 1, wherein the HMG-CoA reductase inhibitor is a compound selected from the group consisting of:

(i) the naphthalene derivatives of formula (II)

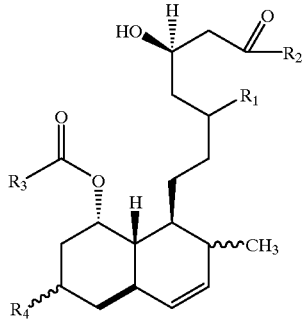

(II)

in which $R_1$ and $R_2$ are a hydroxyl group or alternatively together form an oxygen atom, $R_3$ is a $(C_1-C_{10})$ alkyl, $(C_3-C_{10})$cycloalkyl, $(C_2-C_{10})$alkenyl, phenyl or phenyl$(C_1-C_3)$alkyl group and $R_4$ is hydrogen or a methyl or hydroxyl group;

(ii) the pharmaceutically acceptable salts of the compounds of formula (II) in which $R_1$ and $R_2$ are hydroxyl;

(iii) the indole derivatives of formula (III)

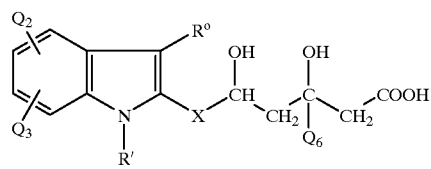

(III)

in which
one of the substituents R° and R' is a group of structure

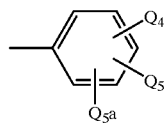

in which $Q_4$ is a hydrogen, chlorine or fluorine atom or a $(C_1-C_4)$alkyl, $(C_1-C_4)$alkoxy (but other than t-butoxy), trifluoromethyl, phenoxy or benzyloxy group, $Q_5$ is a hydrogen, chlorine or fluorine atom or a phenoxy or benzyloxy group and $Q_{5a}$ is a hydrogen, chlorine or fluorine atom or a methyl, ethyl, methoxy or ethoxy group;

and the other substituent R° and R' is a primary or secondary $(C_1-C_6)$alkyl, $(C_3-C_6)$cycloalkyl, benzyl, 2-phenylethyl or 3-phenylpropyl group;

$Q_2$ is a hydrogen, fluorine or chlorine atom or a $(C_1-C_4)$alkyl, $(C_3-C_6)$cycloalkyl, $(C_1-C_4)$alkoxy (but other than t-butoxy), trifluoromethyl, phenoxy or benzyloxy group;

$Q_3$ is a hydrogen, chlorine or fluorine atom or a $(C_1-C_3)$alkyl, $(C_1-C_3)$alkoxy, phenoxy or benzyloxy group;

X is a methylene, ethylene or 1,3-propylene group;

$Q_6$ is a hydrogen atom or a $(C_1-C_3)$alkyl group;

with the limitation that
(1) $Q_5$ and $Q_{5a}$ are hydrogen when $R_4$ is hydrogen,
(2) $Q_{5a}$ is hydrogen when $Q_5$ is hydrogen,
(3) $Q_4$ and $Q_3$ are not at the same time a trifluoromethyl, phenoxy or benzyloxy group,
(4) $Q_3$ is hydrogen when $Q_2$ is hydrogen,
(5) $Q_2$ and $Q_3$ are not at the same time a trifluoromethyl, phenoxy or benzyloxy group;

(iv) the pharmaceutically acceptable esters of the compounds of formula (III), (v) the pharmaceutically acceptable salts of the compounds of formula (III), (vi) the δ-lactones of the compounds of formula (III), (vii) the tetrazole derivatives of formula (IV)

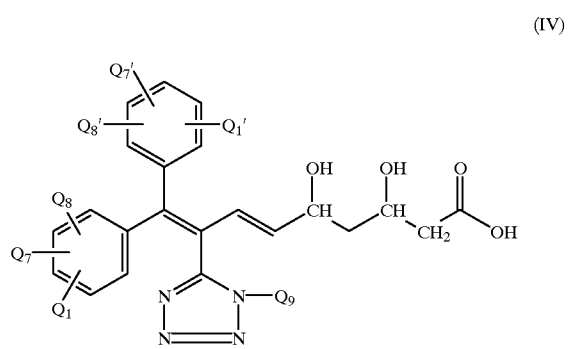

(IV)

in which
$Q_1$ and $Q_1'$ are hydrogen, a halogen or a $(C_1-C_4)$alkyl, $(C_1-C_4)$alkoxy or trifluoromethyl group;

$Q_7$, $Q_7'$, $Q_8$, and $Q_8'$ are hydrogen, a halogen or a $(C_1-C_4)$alkyl or $(C_1-C_4)$alkoxy group;

$Q_9$ is hydrogen or a $(C_1-C_4)$alkyl, $(C_1-C_4)$alkoxyalkyl or (2-methoxyethoxy)methyl group;

(viii) the pharmaceutically acceptable salts of the compounds of formula (IV), (ix) the δ-lactones of the compounds of formula (IV), (x) the pyridine derivatives of formula (V)

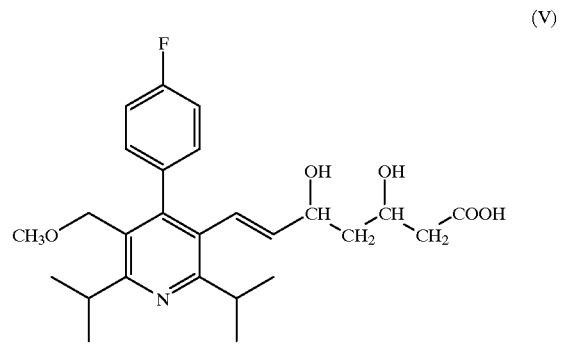

(V)

(xi) the pharmaceutically acceptable salts of the compounds of formula (V), (xii) the δ-lactones of the compounds of formula (V), (xiii) the pyrrole derivatives of formula (VI)

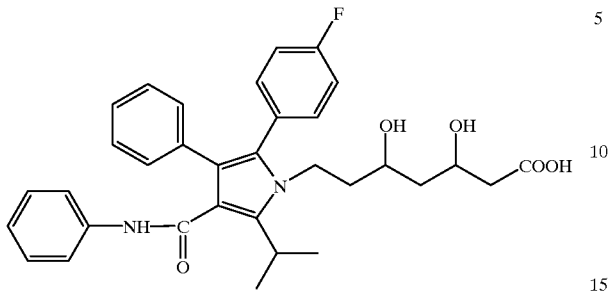

(VI)

(xiv) the pharmaceutically acceptable salts of the compounds of formula (VI), and (xv) the δ-lactones of the compounds of formula (VI).

8. A composition according to claim 7, wherein the HMG-CoA reductase inhibitor is selected from the group consisting of simvastatin, pravastatin sodium, mevastatin, lovastatin, cerivastatin, atorvastatin, an indole derivative of formula (III) in which R° is 4-fluorophenyl, R' is isopropyl, X is ethylene and $Q_2$, $Q_3$ and $Q_6$ are hydrogen, in its racemic or optically active (E) form, the pharmaceutically acceptable salts of the said indole derivative, a tetrazole derivative of formula (IV) in which $Q_1$ and $Q_1'$ are each a fluorine atom and $Q_7$, $Q_7'$, $Q_8$ and $Q_8'$ are hydrogen, in its (E) form of (βR,δS) configuration, and the pharmaceutically acceptable salts of the said tetrazole derivative.

9. A composition according to claim 2, wherein Component (a) is ticlopidine hydrochloride and Component (b) is selected from the group consisting of simvastatin and pravastatin sodium.

10. A composition according to claim 9, which contains from 100 to 250 mg of ticlopidine hydrochloride and from 10 to 40 mg of simvastatin or of pravastatin sodium.

11. A composition according to claim 2, wherein Component (a) is clopidogrel hydrogen sulphate and Component (b) is selected from the group consisting of simvastatin and pravastatin sodium.

12. A composition according to claim 11, which contains from 10 to 75 mg (calculated as free base) of clopidogrel hydrogen sulphate and from 10 to 40 mg of simvastatin or of pravastatin sodium.

13. A method for the treatment of a thromboembolic disorder which comprises administering to a patient in need of such treatment an effective amount of a synergistic composition containing:

(a) a thienopyridine derivative of formula

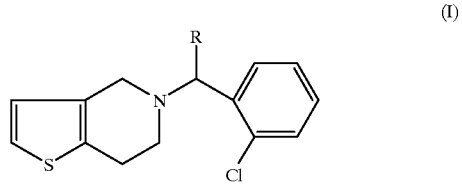

(I)

in which R is hydrogen or a $(C_1-C_4)$alkoxycarbonyl group, or one of its pharmaceutically acceptable salts; and (b) an HMG-CoA reductase inhibitor.

14. A method for the treatment of an atherosclerosis disorder which comprises administering to a patient in need of such treatment a synergistic composition containing:

(a) a thienopyridine derivative of formula

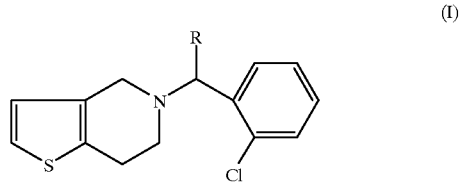

(I)

in which R is hydrogen or a $(C_1-C_4)$alkoxycarbonyl group, or one of its pharmaceutically acceptable salts; and (b) an HMG-CoA reductase inhibitor.

15. A method according to claim 13 wherein component (a) is ticlopidine hydrochloride and component (b) is selected from the group consisting of simvastatin and pravastatin sodium.

16. A method according to claim 13 wherein component (a) is clopidogrel hydrogen sulfate and component (b) is selected from the group consisting of simvastatin and pravastatin sodium.

17. A method according to claim 14 wherein component (a) is ticlopidine hydrochloride and component (b) is selected from the group consisting of simvastatin and pravastatin sodium.

18. A method according to claim 14 wherein component (a) is clopidogrel hydrogen sulfate and component (b) is selected from the group consisting of simvastatin and pravastatin sodium.

* * * * *